(12) United States Patent
Brenneman et al.

(10) Patent No.: US 8,382,697 B2
(45) Date of Patent: Feb. 26, 2013

(54) DEVICES, SYSTEMS, AND METHODS FOR PERIPHERAL ARTERIOVENOUS FISTULA CREATION

(75) Inventors: Rodney Brenneman, San Juan Capistrano, CA (US); Dean A. Schaefer, Aliso Viejo, CA (US); J. Christopher Flaherty, Topsfield, MA (US)

(73) Assignee: Rox Medical, Inc., San Clemente, CA (US)

( * ) Notice: Subject to any disclaimer, the term of this patent is extended or adjusted under 35 U.S.C. 154(b) by 289 days.

(21) Appl. No.: 12/017,437

(22) Filed: Jan. 22, 2008

(65) Prior Publication Data

US 2008/0171944 A1 Jul. 17, 2008

Related U.S. Application Data

(63) Continuation of application No. PCT/US2006/029081, filed on Jul. 26, 2007.

(60) Provisional application No. 60/702,777, filed on Jul. 26, 2005.

(51) Int. Cl.
*A61M 5/00* (2006.01)

(52) U.S. Cl. .......... 604/9; 604/8; 604/6.16; 604/7; 604/10; 604/65; 604/66; 604/67; 604/264; 606/153; 606/157; 606/158; 623/1.1; 623/1.13; 623/1.25

(58) Field of Classification Search .......... 604/8, 9; 606/153, 157, 158; 623/1.1, 1.13, 1.25
See application file for complete search history.

(56) References Cited

U.S. PATENT DOCUMENTS

| | | | | |
|---|---|---|---|---|
| 4,762,128 A * | 8/1988 | Rosenbluth | .......... | 606/192 |
| 4,828,544 A * | 5/1989 | Lane et al. | .......... | 604/9 |
| 5,496,311 A * | 3/1996 | Abele et al. | .......... | 606/28 |
| 5,830,222 A * | 11/1998 | Makower | .......... | 606/159 |
| 6,248,117 B1 * | 6/2001 | Blatter | .......... | 606/153 |
| 6,575,168 B2 * | 6/2003 | LaFontaine et al. | .......... | 128/898 |
| 6,579,311 B1 * | 6/2003 | Makower | .......... | 623/1.23 |
| 6,595,941 B1 * | 7/2003 | Blatter | .......... | 604/4.01 |
| 6,599,303 B1 * | 7/2003 | Peterson et al. | .......... | 606/153 |
| 6,616,675 B1 * | 9/2003 | Evard et al. | .......... | 606/155 |
| 6,827,698 B1 * | 12/2004 | Kleinekofort | .......... | 604/6.06 |
| 6,915,154 B1 | 7/2005 | Docherty et al. | | |
| 7,025,741 B2 * | 4/2006 | Cull | .......... | 604/9 |
| 7,118,546 B2 * | 10/2006 | Blatter | .......... | 604/6.16 |
| 2003/0017150 A1 * | 1/2003 | Torphy | .......... | 424/131.1 |
| 2003/0167030 A1 * | 9/2003 | Weitzel et al. | .......... | 604/8 |
| 2004/0249335 A1 * | 12/2004 | Faul et al. | .......... | 604/9 |
| 2005/0249770 A1 * | 11/2005 | Hunter | .......... | 424/423 |
| 2010/0268316 A1 * | 10/2010 | Brenneman et al. | .......... | 623/1.11 |

FOREIGN PATENT DOCUMENTS

WO WO 97/33522 A1 9/2007

OTHER PUBLICATIONS

International Search Report and Written Opinion of PCT Application No. PCT/US06/29081, dated Apr. 17, 2008, 8 pages total.

* cited by examiner

*Primary Examiner* — Tatyana Zalukaeva
*Assistant Examiner* — Ginger T Chapman
(74) *Attorney, Agent, or Firm* — Wilson, Sonsini, Goodrich & Rosati

(57) ABSTRACT

Devices, systems and methods are disclosed for the formation of an arteriovenous fistula in the limb of the patient. Embodiments include an apparatus for the creation, modification and maintenance of a fistula, including the modification of an existing dialysis fistula; and a method of supplying oxygenated blood to the venous circulation of a patient. A kit of anastomotic implants is described which supports a broad base of patient anatomies and fistula locations. The devices, systems and methods can be used to treat patients with one or more numerous ailments including chronic obstructive pulmonary disease, congestive heart failure, hypertension, hypotension, respiratory failure, pulmonary arterial hypertension, lung fibrosis and adult respiratory distress syndrome.

38 Claims, 8 Drawing Sheets

DEVICES, SYSTEMS, AND METHODS FOR PERIPHERAL ARTERIOVENOUS FISTULA CREATION

CROSS-REFERENCES TO RELATED APPLICATIONS

The present application is a continuation of PCT/US06/29081, filed Jul. 26, 2007, which claimed the priority of U.S. provisional application No. 60/702,777, filed on Jul. 26, 2005, the full disclosures of which are incorporated herein by reference.

BACKGROUND OF THE INVENTION

Field of the Invention

The present invention relates generally to medical devices and methods. More particularly, the present invention relates to devices and methods for creating or modifying a flow of oxygenated blood into the venous system of a patient.

Chronic obstructive pulmonary disease affects millions of patients in the United States alone. The present standard of care is oxygen therapy, which requires a patient to remain near a stationary oxygen source or carry a bulky oxygen source when away from home or a treatment facility. It is easy to appreciate that such oxygen therapy has many disadvantages.

Lung reduction surgery has recently been proposed for treating patients with chronic pulmonary disease. Such surgery, however, is not a panacea. It can be used on only a small percentage of the total patient population, requires long recovery times, and does not always provide a clear patient benefit. Even when successful, patients often continue to require supplemental oxygen therapy.

There is therefore a need for improved approaches, including both devices and methods, for treating patients suffering from chronic obstructive pulmonary disease. If would be desirable if such devices and methods were also useful for treating patients with other conditions, such as congestive heart failure, hypertension, lung fibrosis, adult respiratory distress syndrome, and the like. Such devices and methods should provide for effective therapy, preferably eliminating the need for supplemental oxygen therapy in the treatment of chronic obstructive pulmonary disease. There is a need for simplified procedural methods that limit patient risks and reduce procedure times. Improved Procedures must be developed to apply to a broad base of patient populations that may benefit from the therapy. At least some of these objectives will be met by the invention described hereinafter.

BRIEF SUMMARY OF THE INVENTION

According to a first aspect of the invention, a method of treating a patient with chronic obstructive pulmonary disease (COPD) is disclosed. The distal end of a catheter device is placed into a first vessel of a patient, such as a vein or artery. The distal end of the catheter device is advanced from the first vessel to a second vessel at a location in the limb of the patient, and subsequently withdrawn. A chronic flow of blood between the first vessel and the second vessel is created through a fistula between the two vessels. In a preferred embodiment, the catheter is flexible along a majority of its length, and the distal end of the catheter is intra-luminally advanced down the first vessel, or an additional vessel in luminal communication with the first vessel, prior to the catheter entering the second vessel, such as an advancement over a guidewire that has already been placed between the first vessel and the second vessel. The fistula created may be dilated to improve flow conditions, and preferably an anastomotic implant is placed to enhance long-term patency of the fistula over time. In another preferred embodiment, the original catheter devices places the anastomotic implant after being advanced from the first vessel to the second vessel. The therapeutic benefit of the described method is realized In an alternative embodiment, energy is applied to the fistula, the energy selected from the group consisting of: electrical energy such as radiofrequency or microwave energy; cryogenic energy; heat; radiation; and combinations thereof. In another alternative embodiment, an agent is delivered to the fistula, such as an agent selected from the group consisting of: anti-proliferatives; anti-biotics; antithrombogenics; and combinations thereof. In another embodiment, a flow rate is measured prior to or after the creation of the fistula. Based on the results of the measurement, the fistula creation procedure and/or a fistula modification procedure is adjusted to optimize the therapeutic benefit of the procedure and/or reduce risks or adverse events of the procedure.

In another preferred embodiment, the method further comprises determining the location of the fistula. Numerous diagnostic and information gathering techniques may be employed such as visualization techniques including: angiography; venography; extra-vascular ultrasound; intravascular ultrasound; Doppler ultrasound; and MRI. The fistula site is determined based on one or more of: artery diameter; vein diameter; ratio of artery to vein diameter; distance between the artery and vein lumens; geometric relationship between the artery and vein lumens; distance from an arterial side branch; distance from an venous side branch; arterial flow; venous flow; oxygen content in artery; oxygen content in vein; wall thickness of artery; wall thickness of vein; degree of calcification of artery; degree of calcification of vein; geometric relationship between the artery and vein lumens at the fistula site; hemodynamic factors; other parameters; and combinations thereof.

The method of the present invention provides a medical treatment based on one or more changes to patient physiology including but not limited to: a decrease is systemic vascular resistance; an increase of the partial pressure of $O_2$ dissolved in the arterial blood plasma, an increase of the hemoglobin $O_2$ saturation in arterial or venous blood, an increase of the $O_2$ concentration in arterial or venous blood; and combinations of these. Flow of arterial blood to the venous through the system should exceed 5 ml/min, and is preferably greater than 50 ml/min.

The method of the present invention preferably utilizes a peripheral artery selected from the group consisting of: axillary; brachial; ulnar; radial; profundal; femoral; iliac; popliteal and carotid. The method of the present invention preferably utilizes a peripheral vein selected from the group consisting of: saphenous; femoral; iliac; popliteal; brachial; basilica; cephalic; medial forearm; medial cubital; axillary; and jugular. The resultant fistula may have a circular or an oval cross-section, such as an oval cross-section that has a major axis greater than the diameter of either the artery or vein of the fistula. The method of the present invention preferably utilizes an anastomotic implant placed between the two vessels such as an implant which provides one or more of the following functions: scaffolding an opening between the first vessel and the second vessel; reducing neointimal proliferation into the fistula flow path; preventing tissue from protruding into the fistula flow path; placing a portion of the first vessel wall in tension with the tissue of the second vessel wall; reducing bleeding of the tissue neighboring the fistula;

enhancing healing of the tissue neighboring the fistula; and combinations thereof. In a preferred embodiment, the anastomotic implant includes an active agent, and may also include a covering or partial covering.

According to a second aspect of the present invention, a method of treating chronic obstructive pulmonary disease in a patient is disclosed. The method comprises the creation of a fistula in the limb of the patient, the fistula located between a first anatomical structure and a second anatomical structure. The first anatomical structure contains blood at a first oxygen content level and the second anatomical structure contains blood at a lower oxygen content level. The second anatomical structure provides blood to a lung of the patient. In a preferred embodiment, the fistula is created in a surgical procedure. In an alternative, also preferred embodiment, the fistula is created in a percutaneous, interventional procedure.

In a preferred embodiment, a second fistula is created between a third anatomical structure and a fourth anatomical structure. The third anatomical structure contains blood at a first oxygen content level and the fourth anatomical structure contains blood at a lower oxygen content level. The second fistula is preferably in a limb of the patient.

In yet another preferred embodiment, the method further comprises the placement of a guidewire from the first anatomical structure to the second anatomical structure, such as from an artery to a vein or a vein to an artery. This guidewire can be used to create or modify the fistula utilizing standard interventional "over-the-wire" techniques. In a preferred embodiment, the fistula is dilated to improve flow. In another preferred embodiment, an anastomotic implant is placed within the fistula, such as an implant that is dilated after placement. In yet another preferred embodiment, a second anastomotic implant is placed within the fistula, such as within all or a portion of the first anastomotic implant. In yet another preferred embodiment, energy or an active agent is applied to the fistula to improve the therapeutic benefit and/or enhance long-term effectiveness.

In yet another preferred embodiment, the method further comprises the performance of flow measurement procedure, such as a measurement made prior to or after the creation of the fistula. Based on the measurement, the fistula site may be chosen or altered, or an already created fistula may be modified such as via a dilation procedure or the placement of an anastomotic implant. In yet another preferred embodiment, the method further comprises the determination of the fistula location. Additional diagnostic procedures may be performed prior to or during the fistula creation procedure, such as a vessel visualization procedure including but not limited to: angiography; venography; extra-vascular ultrasound; intra-vascular ultrasound; Doppler ultrasound; and MRI. The fistula location is determined based on an analysis of a parameter selected from the group consisting of: artery diameter; vein diameter; ratio of artery to vein diameter; distance between the artery and vein lumens; geometric relationship between the artery and vein lumens; distance from an arterial side branch; distance from an venous side branch; arterial flow; venous flow; oxygen content in artery; oxygen content in vein; wall thickness of artery; wall thickness of vein; degree of calcification of artery; degree of calcification of vein; geometric relationship between the artery and vein lumens at the fistula site; hemodynamic factors and combinations thereof.

The method of the present invention provides a medical treatment based on one or more changes to patient physiology including but not limited to: a decrease is systemic vascular resistance; an increase of the partial pressure of $O_2$ dissolved in the arterial blood plasma, an increase of the hemoglobin $O_2$ saturation in arterial or venous blood, an increase of the $O_2$ concentration in arterial or venous blood; and combinations of these. Flow of arterial blood to the venous through the system should exceed 5 ml/min, and is preferably greater than 50 ml/min.

The method of the present invention preferably utilizes a peripheral artery selected from the group consisting of: axillary; brachial; ulnar; radial; profundal; femoral; iliac; popliteal and carotid. The method of the present invention preferably utilizes a peripheral vein selected from the group consisting of: saphenous; femoral; iliac; popliteal; brachial; basilica; cephalic; medial forearm; medial cubital; axillary; and jugular. The resultant fistula may have a circular or an oval cross-section, such as an oval cross-section that has a major axis greater than the diameter of either the artery or vein of the fistula. The method of the present invention preferably utilizes an anastomotic implant placed between the two vessels such as an implant which provides one or more of the following functions: scaffolding an opening between the first vessel and the second vessel; reducing neointimal proliferation into the fistula flow path; preventing tissue from protruding into the fistula flow path; placing a portion of the first vessel wall in tension with the tissue of the second vessel wall; reducing bleeding of the tissue neighboring the fistula; enhancing healing of the tissue neighboring the fistula; and combinations thereof. In a preferred embodiment, the anastomotic implant includes an active agent, and may also include a covering or partial covering.

According to a third aspect of the present invention, a method of treating chronic obstructive pulmonary disease in a patient is disclosed. The method comprises the modification of a pre-existing dialysis fistula. In a preferred embodiment, the flow rate of the dialysis fistula is modified, such as a flow reduction procedure including the placement of an intra-luminal or extra-luminal device that narrows a portion of the flow path to reduce flow. In a preferred embodiment, the dialysis fistula includes an artificial graft, and the artificial graft lumen is narrowed to reduce flow. In an alternative embodiment, the existing fistula flow rate is increased such as via a dilation procedure.

According to a fourth aspect of the present invention, a method of selecting an anatomical location for a fistula to be created between an artery and a vein is disclosed. The fistula is created to treat chronic obstructive pulmonary disease. The selection method includes the performance of a vessel visualization procedure and measuring one or more of the following at a proposed fistula location: artery diameter; vein diameter; ratio of artery to vein diameter; distance between the artery and vein lumens; geometric relationship between the artery and vein lumens; distance from an arterial side branch; distance from an venous side branch; arterial flow; venous flow; oxygen content in artery; oxygen content in vein; wall thickness of artery; wall thickness of vein; degree of calcification of artery; degree of calcification of vein; geometric relationship between the artery and vein lumens at the fistula site; hemodynamic factors and combinations thereof.

According to a fifth aspect of the present invention, a kit for creating a fistula to treat chronic obstructive pulmonary disease is disclosed. The kit includes an anastomotic implant that is selected from the group consisting of a first anastomotic implant and a second anastomotic implant. The first anastomotic implant is for placement in a fistula between an anatomical structure containing oxygenated blood and an anatomical structure supplying blood to a lung of the patient. The kit further includes a second anastomotic implant for placement in a fistula between an anatomical structure containing oxygenated blood and an anatomical structure supplying blood to a lung of the patient. The first anastomotic implant and the second anastomotic implant have different geometries, and either the first anastomotic implant or the second anastomotic implant is implanted based on an analysis of one or more patient parameters. In a preferred embodiment, the implant is chosen based on one or more of the following: artery diameter; vein diameter; distance between the artery and vein lumens; distance from an arterial side branch; distance from an arterial side branch; arterial flow; venous flow; oxygen content in artery; oxygen content in vein; wall thickness of artery; wall thickness of vein; degree of calcification of artery; degree of calcification of vein; geometric relationship between the artery and vein lumens at the fistula site; hemodynamic factors; and combinations thereof.

Both the foregoing general description and the following detailed description are exemplary and are intended to provide further explanation of the embodiments of the invention as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention.

In the drawings.

DETAILED DESCRIPTION OF THE INVENTION

Reference will now be made in detail to the present embodiments of the invention, examples of which are illustrated in the accompanying drawings. Wherever possible, the same reference numbers will be used throughout the drawings to refer to the same or like parts.

Figure 1:
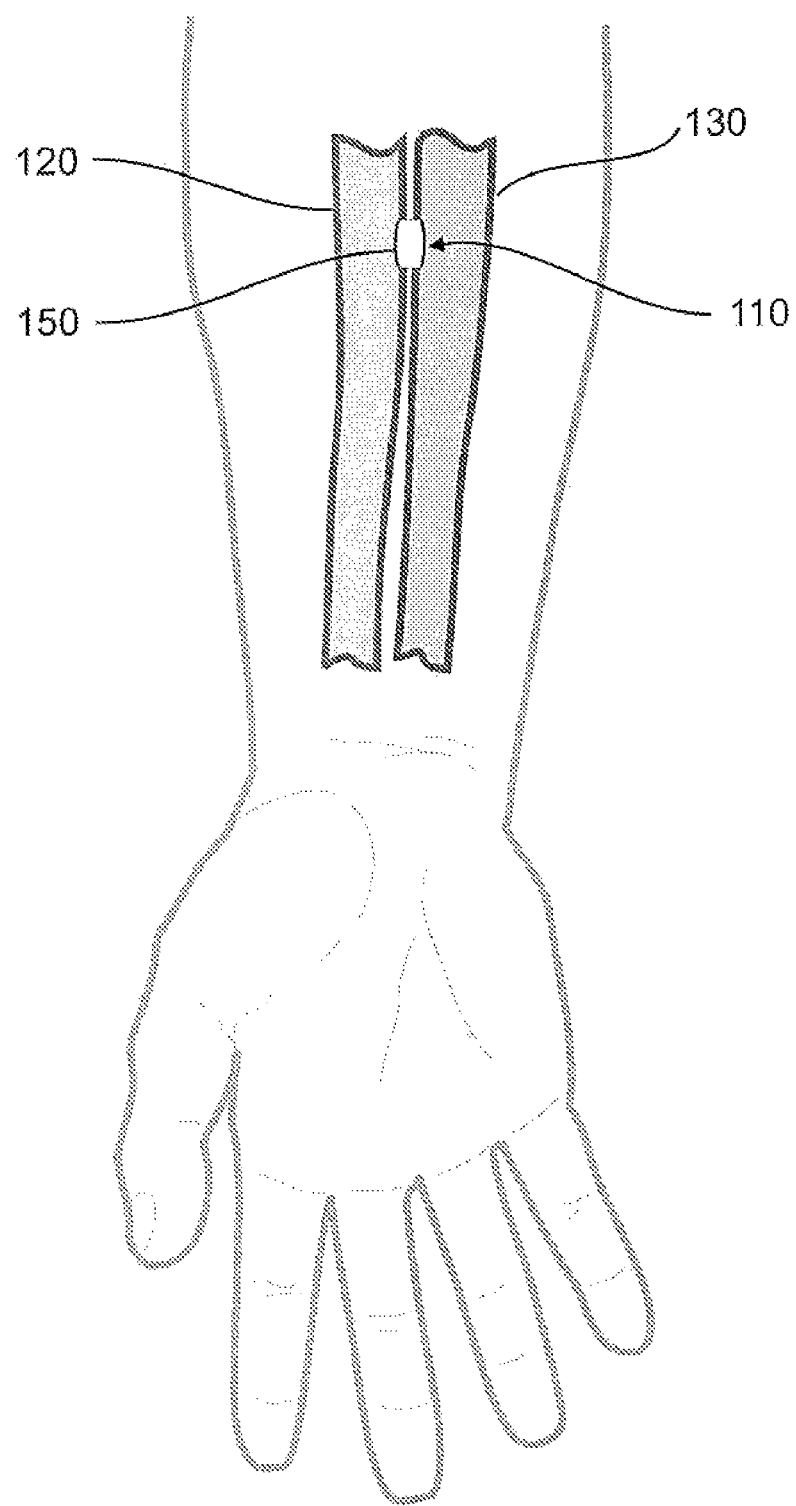
FIG. 1 illustrates a fistula, created in the forearm of the patient, consistent with the present invention.

FIG. 1 depicts a peripheral arteriovenous fistula, fistula 110, created in a patient, such as a human or other animal, between artery 130 and vein 120. Fistula 110 is located in the patient's forearm and provides oxygenated blood from the higher-pressure arterial system to the venous system such that blood flows from the artery 130 to vein 120 through and fistula 110. The fistula may be created in one or more of a set of numerous locations in the body of the patient, preferably in a limb to avoid unnecessary trauma and risk to a major, central vessel such as the Aorta and Vena Cava. Applicable arteries for fistula 110 include but are not limited to: axillary; brachial; ulnar; radial; profundal; femoral; iliac; popliteal; and carotid, preferably at a location where the artery is approximately 4 mm or less in diameter and at least 2 mm in diameter. Applicable veins for fistula 110 include but are not limited to: saphenous; femoral; iliac; popliteal; brachial; basilica; cephalic; medial forearm; medial cubital; axillary; and jugular, preferable at a location where the vein is at least 4 mm in diameter or less and at least 3 mm in diameter. Fistula 110 is preferably at a location wherein the two vessel walls are within 20 mm of one another, preferably less than 10 mm apart.

The forearm located arteriovenous fistula 110 of FIG. 1 is maintained in a fluidly open state by way of a vessel anastomotic clip, shunt device 150. In alternative, also preferred embodiments, a fistula is created without an anastomotic clip, such as a fistula created with the placement of surgical sutures in an end-to-side or side-to-side anastomosis of vessels. Numerous devices and methods can be employed to create the fistula of the present invention, such as vessel-to-vessel flow-channel creating devices including radio-frequency ablation and/or coagulation devices, and artificial blood flow conduits including PTFE grafts. In another preferred embodiment, an existing dialysis fistula is modified to provide a therapeutic benefit other than dialysis access, such as treatment of a heart condition including COPD. Flow in the existing dialysis fistula may be decreased, such as with the placement of an intra-luminal narrowing implant or extra-luminal impinging device, when the fistula is no longer to be accessed for dialysis, to improve therapeutic benefit for the heart condition. Dialysis fistulas utilizing the radial artery typically reach of flow rate between 600-1200 ml/min, which may be above the desired flow rate for the method of the current invention. Flow reduction procedures, as are described in detail hereinbelow, are appropriate for converting these fistulas from a dialysis therapy fistula to a COPD therapy fistula.

Shunt device 150 is manufactured from one or more bio-compatible materials and can provide numerous functions. Shunt device 150 can provide tension between artery 130 and vein 120 at the fistula site to create a temporary or long-term fluid seal between the tissue surrounding the openings in each vessel wall. Shunt device 150 can provide sufficient radial force, either temporary or long-term, to maintain a lumen between artery 130 and vein 120, such as a lumen with a relatively circular cross section or an oval cross section. An oval cross section allows a larger cross sectional area such as that of an oval that has a major axis longer than the diameter of either the vein or artery at the fistula location. Shunt device 150 can act as a depot for one or more pharmaceutical or other agents such as to enhance long-term patency and biocompatibility. Also, shunt device 150 can provide a control means to adjust the flow of blood from the arterial system to the venous system, either automatically or in combination with a separate device. Shunt device 150 can provide other functions such as to enhance the resultant therapeutic benefit of fistula 110 and/or prevent or reduce undesired side effects such as thrombus or atheroma formation, neointimal proliferation, vessel erosion and/or other adverse conditions.

Shunt device 150 has been placed in a surgical or interventional procedure, or a combination of the two. In an open surgical procedure, a clinician use scalpels and other cutting means to expose the associated vessels to create fistula 110. Alternative, minimally invasive surgical procedures make use of one or more tubes, placed through small incisions in the skin, through which the clinician can pass various visualization and surgical tools to create the connection between the artery 130 and vein 120. In an interventional procedure, similar to balloon angioplasty and interventional atherectomy procedures, catheter devices are placed through introducer tools into one or more vessels, and advanced through the vasculature to a specific location by guided fluoroscopy, ultrasound or other imaging equipment.

The flow of oxygenated blood from the arterial system through fistula 110 to the venous system can provide therapeutic benefit to patients suffering from one or more diseases including but not limited to: chronic obstructive pulmonary disease, congestive heart failure, hypertension, hypotension, respiratory failure, pulmonary arterial hypertension, lung fibrosis and adult respiratory distress syndrome. The therapeutic benefit results from one or more factors as is described hereinbelow.

Blood returning to the right side of the heart is pumped to the lungs where is becomes oxygenated or re-oxygenated before returning to the left side of the heart to be pumped to the body's tissues via the arterial system. Blood flow experiences a resistance from all of the system vasculature, which is referred to as systemic vascular resistance (SVR). The recirculated blood that passes through shunt device 150 bypasses the peripheral microcirculation and decreases the SVR. To achieve therapeutic benefit, a decrease of SVR of at least 5% would be desired. Additional or alternative changes to patient physiology that may provide a therapeutic benefit include but are not limited to: an increase of the partial pressure of $O_2$ dissolved in the arterial blood plasma, an increase of the hemoglobin $O_2$ saturation in arterial or venous blood, an increase of the $O_2$ concentration in arterial or venous blood; and combinations of these.

Blood flows through shunt device 150 from artery 130 to vein 120 because of the pressure gradient between the blood in the arterial system and the blood in the venous system. In a preferred embodiment, the flow through shunt device 150 is at least 5 ml/min, and preferably greater than 50 ml/min. It may be desirable for shunt device 150 to self-regulate flow, or be controllable via internal or external means, as will be described in reference to subsequent figures hereinbelow. The flow of arterial blood into vein 120 has cardiac, circulatory and respiratory effects. Cardiac output increases with a decrease in SVR due to the increased pressure gradient. This increase in cardiac output could benefit patients with cardiac failure or patients who suffer from low cardiac output, such as congestive heart failure patients.

Regarding respiratory effects, the oxygenated blood that mixes with the venous blood already present in vein 120 results in a higher $O_2$ concentration venous blood entering the right atrium of the heart and eventually the lungs. This high $O_2$ concentration venous blood leads to an increase in the $O_2$ concentration in arterial blood in two ways: (1) since the blood that is shunted does not have $O_2$ extracted by tissue capillaries, the blood returning to the lungs has a higher $O_2$ concentration after the creation of the shunt than before, and (2) the binding of $O_2$ to the hemoglobin component of blood is more efficient with a higher Pa $O_2$ (partial pressure of $O_2$ in arterial plasma) resulting in increased oxygen carrying capacity. These advantageous respiratory effects could benefit patients with pulmonary arterial hypertension by lowering pulmonary arterial blood pressure, patients with heart or respiratory failure by increasing arterial oxygen concentration, or patients with chronic obstructive pulmonary disease by increasing blood oxygen concentration.

Regarding circulatory effects, another important benefit of decreasing SVR is related to the fact that the lungs regulate their blood flow according to the $O_2$ content. An increase in the $O_2$ content should decrease the pulmonary arterial blood pressure. These advantageous circulatory effects could benefit patients with hypertension by lowering systemic arterial, systolic and/or diastolic blood pressure. These cardiac, respiratory and circulatory effects could also benefit numerous other patients with circulatory or other diseases including but not limited to: hypotension (by increasing cardiac output), lung fibrosis, adult respiratory distress syndrome, and the like.

Various interventional techniques can be used to create a fistula at or near an artery and a vein a limb of the patient, such as in the forearm as is depicted in FIG. 1. In a preferred method, a fistula is created between a starting vessel and a target vessel, wherein the starting vessel and target vessel consist of an artery and a vein or a vein and an artery, respectively. An arterial catheter is placed in the artery, and a venous catheter is placed in the Vein, at a location upstream of the fistula creation site. A crossing needle device that incorporates a hollow needle, advancable with controls at the device's proximal end, is placed in the starting vessel, either an artery or a vein. Radiographic dye, or other contrast medium is injected through the catheter in the target vessel. The crossing needle of the crossing needle device is advanced, the needle penetrating first the wall of the starting vessel and then the wall of the target vessel, eventually with the tip of the needle residing within the lumen of the target vessel. A guidewire is passed through the crossing needle down the lumen of the target vessel. An anastomotic clip delivery system, which may be the same as the crossing needle device or a separate catheter, is advanced over the previously placed guidewire, and used to place an anastomotic clip between the starting vessel and the target vessel.

Figure 2:
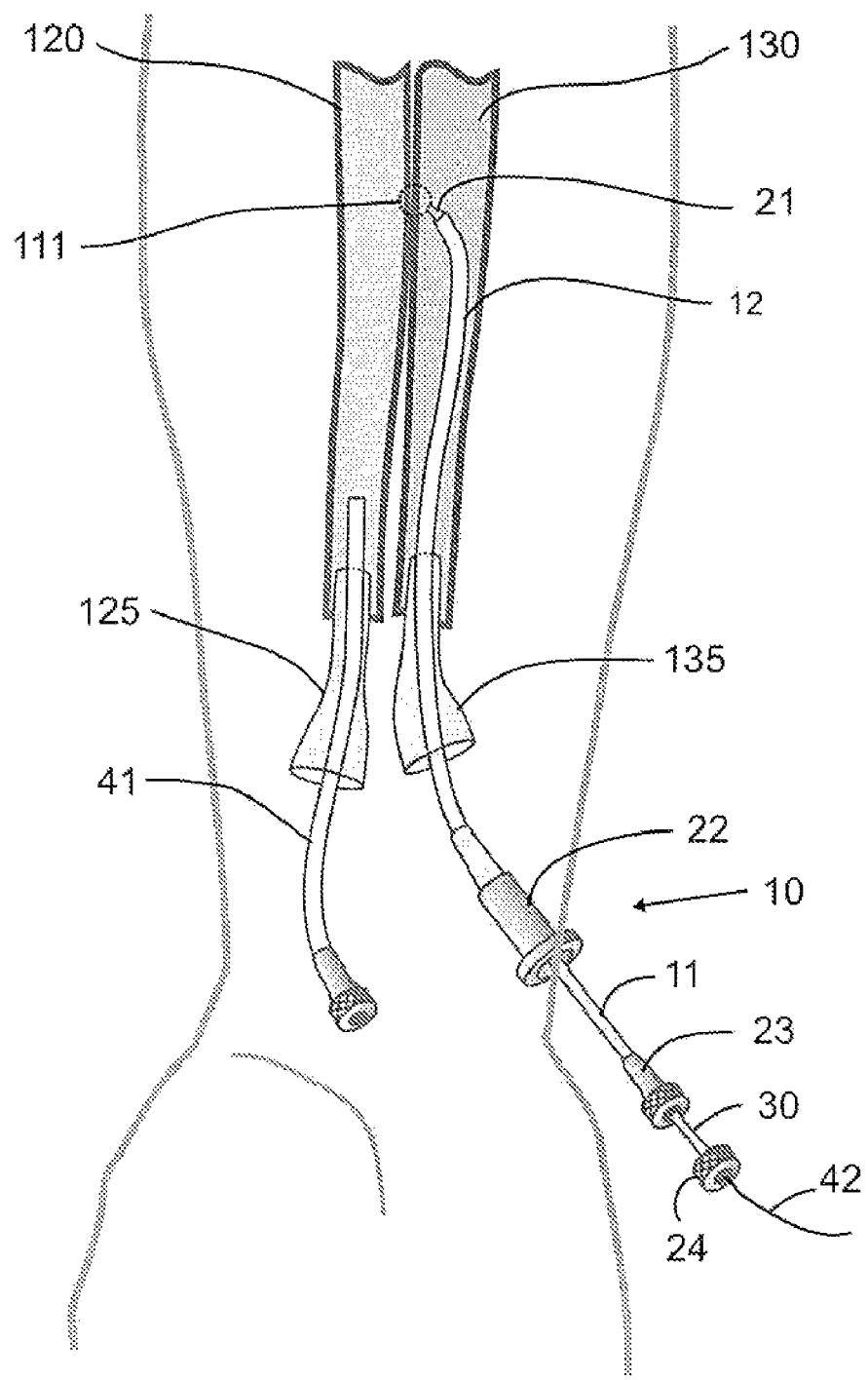
FIG. 2 illustrates fistula creation apparatus and method consistent with the present invention.

Referring to FIGS. 2 through 9, a method of creating a peripherally located fistula is described. Depicted in FIG. 2 is artery 130 and vein 120, which travel to at least one location wherein their vessel walls are in relative proximity to each other, such as within 20 mm of each other. An introducer sheath, venous introducer 125 is placed through the skin of the patient, to provide access to Right Venous Iliac 122. A venous catheter, imaging catheter 41, used for injecting contrast medium and other agents, as well as the passage of guidewires and other devices through an inner lumen, is placed through venous introducer 125 so that its tip resides upstream to the intended location for the fistula, fistula site 111. This tip location allows radiographic dye or other contrast medium injected through imaging catheter 41 to travel, with the venous blood flow, past fistula site 111 and toward the heart of the patient. Fistula site 111 is preferably chosen, at least in relative proximity, prior to any incisions in the patient's skin. A non-invasive vessel visualization procedure, such as through the use of external ultrasound, allows numerous measurements to be performed including: visualization of vessel proximity and other geometric relationships between vessels and their lumens; vessel lumen diameter; vessel wall thickness and presence of calcification and other intra-luminal blockages; presence and relative location of vessel side-branches and bifurcations; and even blood flow rates through the use of Doppler ultrasound. Other applicable forms of vessel visualization, with or without prior an invasive procedure, includes: angiography; venography; X-ray; internal ultrasound including intravascular ultrasound; and magnetic resonance imaging (MRI). Other diagnostic procedures, in addition to the visualization procedures, may be performed to determine a location of the fistula of the present invention, including a measurement of one or more blood parameters near the intended fistula location site 111, such as the amount of dissolved oxygen in the blood passing near the location.

A method of choosing the location for fistula site 111 is intended to maximize therapeutic benefit, simplify the fistula creation procedure, improve long-term patency of the fistula, and/or reduce adverse events and undesired side effects. A preferred method includes an analysis of one or more of: artery diameter; vein diameter; ratio of artery to vein diameter; distance between the artery and vein lumens; distance from an arterial side branch; distance from a venous side branch; arterial flow; venous flow; oxygen content in artery; oxygen content in vein; wall thickness of artery; wall thickness of vein; degree of calcification in artery; degree of calcification in vein; hemodynamic factors, and other factors.

A second introducer sheath, arterial introducer 135 is placed through the skin of the patient and into the artery. Catheter apparatus 10 is inserted through arterial introducer 135 and advanced to a location proximate fistula creation site 111, such as at a starting location near the intended fistula creation site 111, or remote from site 111 such as percutaneously entering a different artery and advanced to the intended artery. Catheter apparatus 10 can provide numerous functions including but not limited to: injection of contrast medium including radiographic dyes and ultrasonic medium, injection of drugs or other agents, aspiration of blood, vessel to vessel needle advancement, visualization of internal structures such as via ultrasound, fistula and/or implant dilation, fistula and/or implant contraction, tissue debulking, placement of an anastomotic clip, removal of an anastomotic clip, passage of guidewires and other small diameter devices, placement of a fistula treatment device, placement of a anastomotic clip treatment device, placement of a flow modification device, placement of a visualization device such as an intravascular ultrasound catheter and other functions. These various functions can be performed by or with the assistance of apparatus 10 through the use of functional elements integrated into apparatus 10, or separate devices which can be passed through one or more lumens accessible from the proximal end of apparatus 10.

Located at the proximal end of apparatus 10 are various knobs that are used to rotate, advance, retract, manipulate, activate, or otherwise control the slidable tubes, needles and other elements of apparatus 10. Sheath advancement knob 22 is mechanically connected to outer sheath 12 that surrounds various internal tubes, elements and lumens. In a preferred embodiment, apparatus 10 includes a visualization element, such as an ultrasound element, not shown. The visualization element can produce, through electronic or other means, a visual representation of the device and neighboring tissue. The visualization element may be an ultrasound catheter, such as a rotational or fixed array ultrasound catheter, which creates a cross-sectional image of the area surrounding the device. The ultrasound catheter can be inserted into a lumen of apparatus 10, or may be an integrated ultrasound device that has as an array of ultrasound crystals which are fixedly mounted along the distal portion of apparatus 10 and contain electronic connections that are connected to a proximal handle of apparatus 10, these connections mating with a standard ultrasonic viewing monitor. In an alternative or additional, preferred embodiment, apparatus 10 includes one or more visualization markers, such as radiographic markers or embedded agents such as barium sulfate, or ultrasonically visible markers, all not shown. These markers can be used to perform controlled advancements, retractions, rotations and other positioning of apparatus 10 during the fistula creation procedure.

An internal tube, core 11 is slidingly received within outer sheath 12 and advancable and retractable through manipulation of core advancement knob 23. Core 11 has at its distal end, tip 21, which preferably has a dilating tip shape, and is atraumatic. Tip 21 is advanced to fistula site 111, by advancing apparatus 10 through arterial introducer 135. Within core 11 is another tubular device, a flexible, advancable needle, needle 30 that has attached at its proximal end, needle advancement knob 24. Slidingly received within needle 30 is a standard interventional guidewire, guidewire 42. Needle 30 may consist of an outer protective sheath, not shown, with a flexible, advancable needle contained within its lumen.

Tip 21 is positioned against the wall of artery 130 such that needle 30 can be advanced from an artery, artery 130, to a vein, vein 120. In an alternative, preferred embodiment, the procedure is performed from vein to artery, such as from vein 120 to artery 130. Prior to advancing needle 30 out of tip 21, radiographic dye can be injected to visualize the border of the starting vessel, artery 130, under fluoroscopy. An injection of contrast medium from a catheter in the target vessel can visualize the border of the target vessel walls as well. Contrast medium can be injected through the lumen in needle 30, or via a separate lumen incorporated through the length of apparatus 10.

In the artery to vein approach depicted in FIGS. 2 through 5, the outer sheath 12 can be positioned against the arterial wall, such as by deflection means integral to apparatus 10, to provide support and directionality as needle 30 is advanced. Typical advancement distance of needle 30 is at least 2 mm, which can be controlled with markings or other control means located on the proximal end of apparatus 10, not shown. After the needle 30 is advanced, or partially advanced, a contrast medium injection can be performed through the lumen in needle 30, to confirm access of the target vessel, vein 120.

Figure 3:
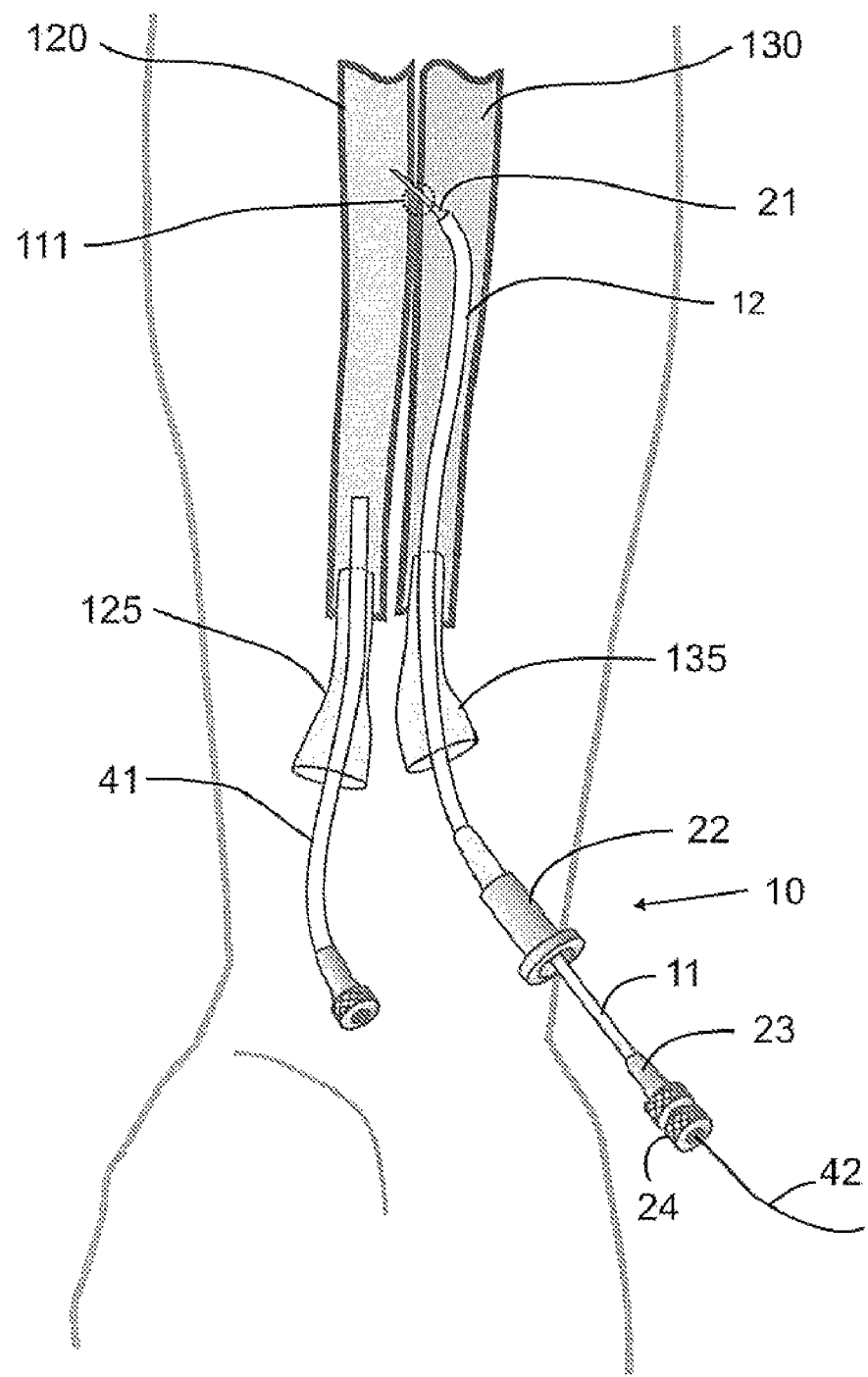
FIG. 3 illustrates fistula creation apparatus and method consistent with the present invention.

Referring now to FIG. 3, needle 30 has been advanced from artery 130 into vein 120 by advancing needle advancement knob 24. Advancement can be rapid, such as via a needle injection mechanism incorporated into a proximal handle of apparatus 10, injection mechanism not shown, and the injection can be performed in a single continuous advancement or in multiple discrete steps. In the discrete step approach, access of the target vessel can be confirmed by repeat attempts at advancing or probing of guidewire 42, and/or by injection of contrast medium through the lumen of needle 30 and/or by aspiration of blood through needle 30. Visual examination of blood color can indicate arterial or venous blood withdrawn to confirm access to artery or vein respectively. When properly accessed, the distal portion of guidewire 42 can be advanced from artery 130 into vein 120, in either a superior or inferior direction.

Figure 4:
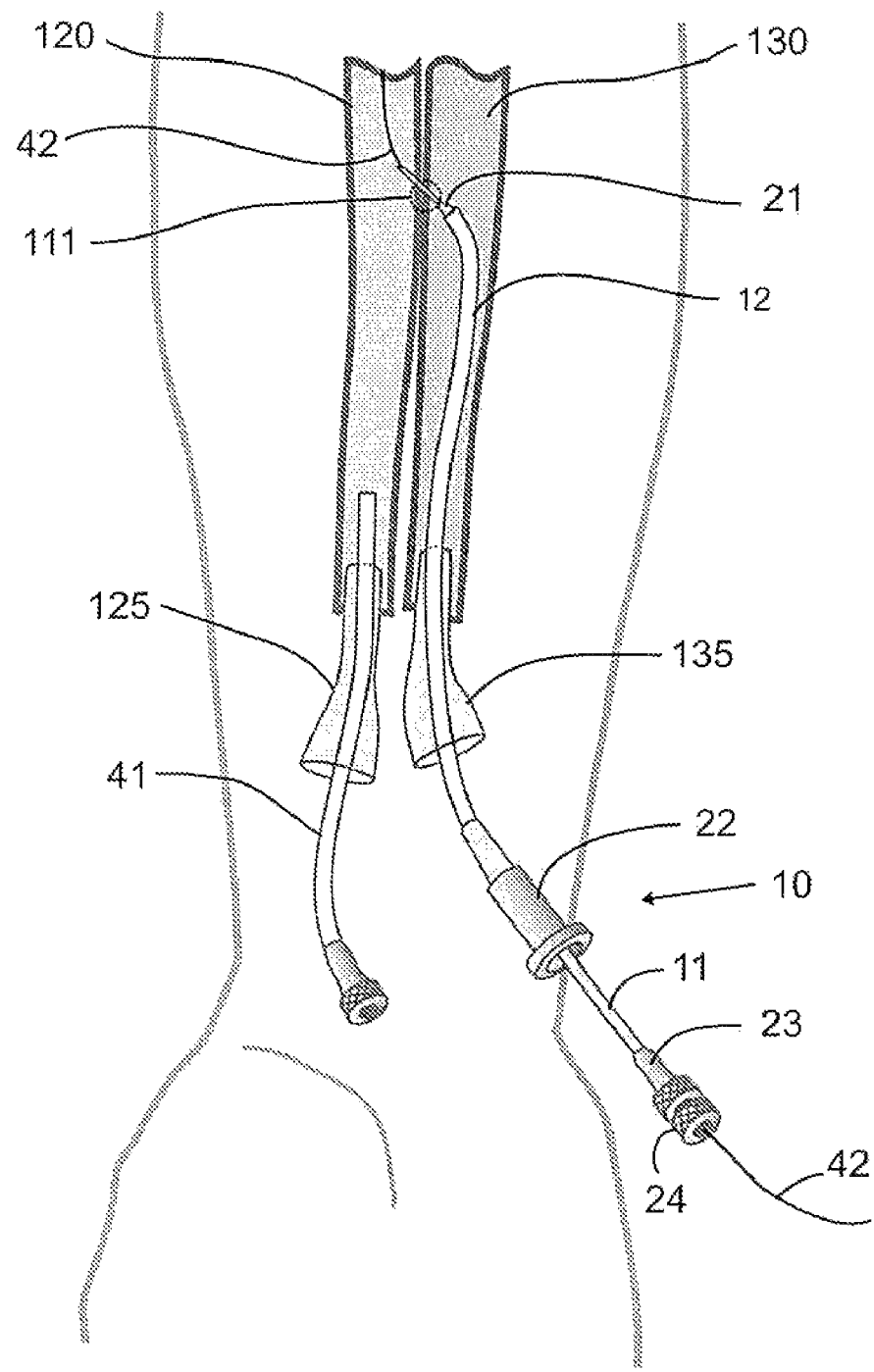
FIG. 4 illustrates fistula creation apparatus and method consistent with the present invention.

Referring now to FIG. 4, guidewire 42 has been advanced in a superior direction into vein 120. Needle 30 is ready to be retracted, and depending on the configuration of apparatus 10, either removed entirely from a lumen of apparatus 10 or retracted to a less distal location but remaining within apparatus 10. In a preferred embodiment, an automatic retraction mechanism, such as a spring-loaded mechanism, not shown, is integral to apparatus 10. In various preferred embodiments of the present invention, outer sheath 12 and its internal components are removed, and a second catheter device of apparatus 10 is inserted over guidewire 42 to place an anastomotic clip. In alternative preferred embodiments of the present invention, outer sheath may be removed or partially removed, to load an anastomotic clip delivery device. In another preferred embodiment, apparatus 10 and outer sheath 12 remain at the location proximate fistula site 111, and an anastomotic clip delivery device is available, either by being already in place, or loaded within a lumen of outer sheath 12. In a preferred embodiment, an anastomotic clip delivery device is inserted after needle 30 is removed from the lumen of outer sheath 12.

Figure 5:
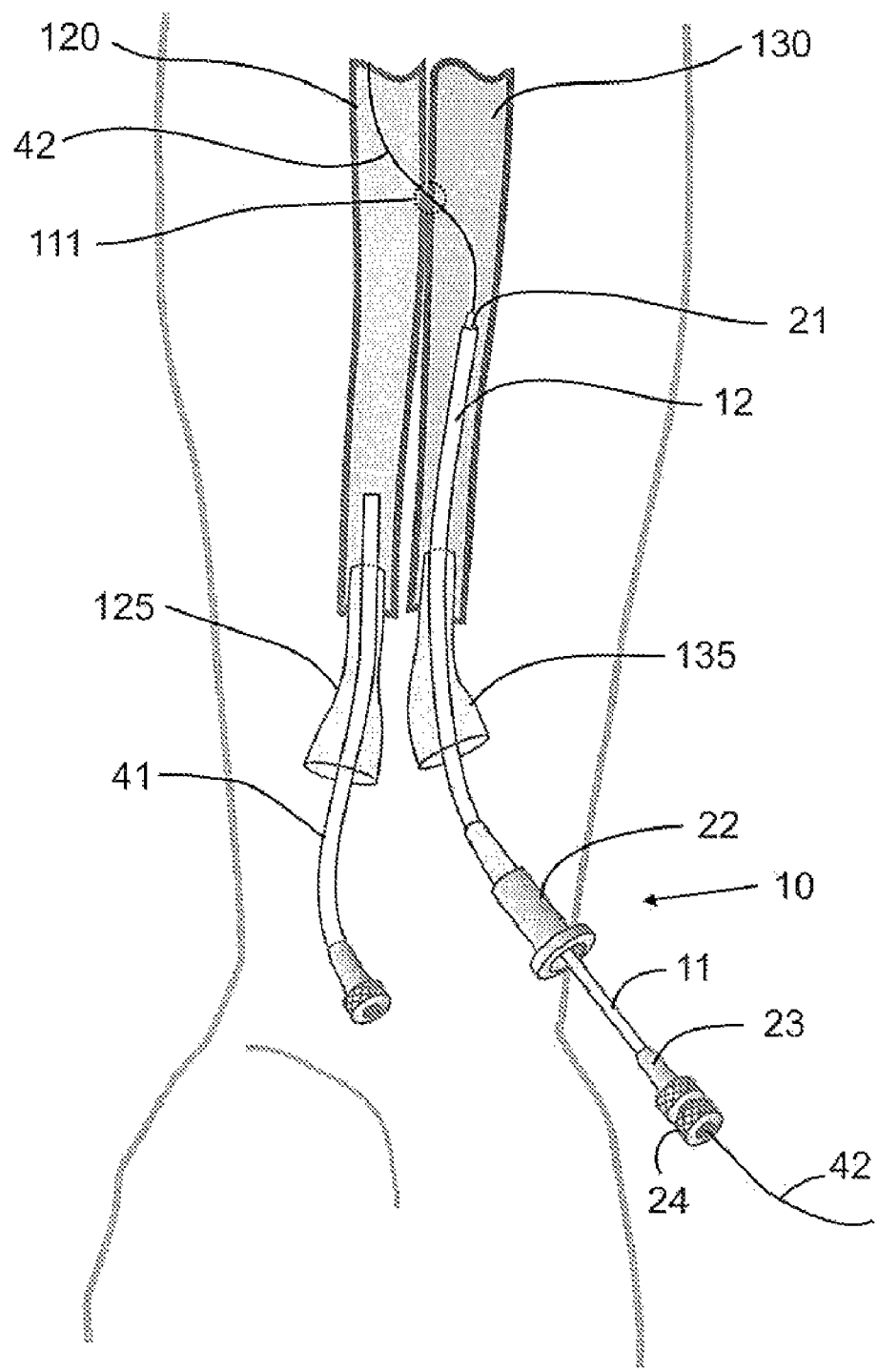
FIG. 5 illustrates fistula creation apparatus and method consistent with the present invention.

FIG. 5 depicts catheter 10 in a partially withdrawn position, the retraction being performed while maintaining and/or advancing guidewire 24 such that a sufficient portion of guidewire 24 remains within vein 120. In a preferred embodiment, catheter 10 is fully withdrawn, leaving guidewire 24 sufficiently advanced into vein 120, after which a separate catheter is inserted over-the-wire to place an anastomotic clip. In an alternative embodiment, catheter 10 includes the anastomotic clip and an externally operable deployment mechanism. Prior to the placement of the anastomotic clip, the tissue between the lumens of the artery 130 and vein 120, such as the vessel wall tissues and tissue external to the walls, may need to be expanded or dilated with one or more devices such as a standard angioplasty balloon. Alternatively or additionally, it may be desirous to remove a portion of this tissue utilizing one or more debulking tools such as ablative tools or tissue cutting and removing tools. These various methods of enlarging the opening, or flow path, between the two vessels can be performed with catheter 10 or a separate catheter; over needle 30 or over a needle assembly, not shown; over guidewire 42 after needle 30 or a needle assembly is retracted; or combinations of these.

Apparatus 10 may include various flow path or channel creation means, described in more detail in reference to subsequent figures. Flow path dilation elements may include the incorporation of a compliant or non-compliant balloon, with an inflation lumen and port located on the proximal end of apparatus 10, all not shown. The balloon may be integrated into a distal portion of the needle assembly, on a distal portion of outer sheath 12, on a distal portion of core 11, or on a separate tubular device advancable through a lumen of apparatus 10, all not shown. Debulking means may include one or more of an energy ablation device, such as a radiofrequency ablation element, either monopolar or bipolar, or a cutting element similar to a pull back cutting element used in pull back atherectomy procedures. The debulking means can be advanced from the starting vessel to the target vessel to perform the debulking procedure, advanced to the target vessel first and then pulled back from the target vessel to the starting vessel to perform the debulking procedure, or both. In all flow path creation and enlargement procedures, the flow path creation and enlargement elements can be integrated into one or more components of apparatus 10 or be included in a separate tubular structure advancable through a lumen of apparatus 10. These flow path creation and enlargement procedures are all performed over the guidewire placed from the starting vessel to the target vessel.

Figure 6:
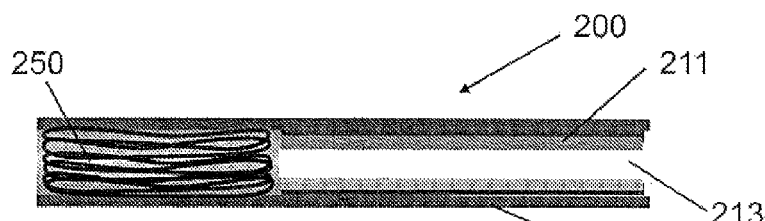
FIG. 6 is a cross sectional view of an anastomotic clip deployment device and method consistent with the present invention.

FIG. 6 depicts apparatus 200, an anastomotic clip deployment apparatus consistent with the present invention. Apparatus 200 is a flexible, catheter device, which includes a sliding core, core 211, which has a lumen, lumen 213, from its proximal end, not shown, to its distal end, to allow placement over a guidewire, such as guidewire 42 placed in FIGS. 2 through 5 in the forearm of the patient. In an alternative embodiment, apparatus 200 may include a rigid portion along a majority of its length. Apparatus 200 includes outer sheath 212, which surrounds and slidingly receives core 211. Located at or near the distal end of apparatus 200, is a preloaded anastomotic clip, clip 250, which is a self-expanding device constrained by outer sheath 212 which can be deployed to secure and create a fistula between an artery and a vein, such as an artery and vein in the forearm or the patient consistent with the method continued from FIGS. 2 through 5, or at another location such as the thigh of a patient or other peripheral vascular location. Clip 250 can be deployed by advancing core 211 forward while maintaining outer sheath 212 in a relatively fixed position; by retracting sheath 212 while maintaining core 211 in a relatively fixed position; or by both advancing core 211 and retracting outer sheath 212. A deployment trigger and trigger mechanism, not shown, may be incorporated into apparatus 200 such that the retraction and/or advancement steps are accomplished by activating the trigger, such that timing, relative timing, and advancement and retraction distances are predetermined by the trigger mechanism. In a preferred embodiment, some amount of advancement and retraction are accomplished simultaneously.

Figure 7:
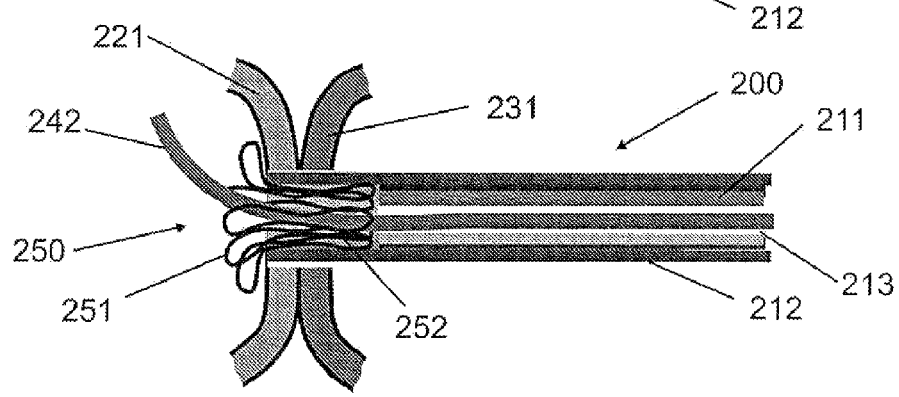
FIG. 7 is a cross sectional view of an anastomotic clip deployment device shown at a fistula creation site prior to full deployment of an anastomotic clip.

FIG. 7 depicts apparatus 200 deployed over a guidewire, guidewire 242, which can be placed similar to guidewire 42 of FIGS. 2 through 5, such that it passes from a vein and artery in the forearm of a patient. Guidewire 242 is shown passing through arterial wall 231, and venous wall 221. Outer sheath 212 is shown passing through both arterial wall 231 and venous wall 221 to assist in the deployment of clip 250. In order to cross through the vessel walls, apparatus 200 may include a flow path-enlarging element such as an integrated balloon element; and/or apparatus 200 may include a dilating slope on one or more distal ends. Apparatus 200 of FIG. 7 depicts clip 250 being placed from artery to vein, however it should be appreciated that a vein to artery placement can be similarly accomplished by apparatus 200 and would result in a similarly placed clip 250.

In FIG. 7, catheter 200 is inserted over a guidewire, guidewire 242, such as a guidewire placed from a first vessel to a second vessel as described in reference to FIGS. 2 through 5. In an alternative embodiment, catheter 200 can be inserted without guidewire 242, such as through the use of visualization or other percutaneous techniques. Shown in FIG. 7, clip 250 is partially deployed with distal end 251 of clip 250 expanded and pulled against venous wall 221. Deployment is initiated such as by advancing core 211 while maintaining outer sheath 212 in a fixed position; by retracting sheath 212 while maintaining core 211 in a fixed position; or by both advancing core 211 and retracting sheath 212, preferably in a simultaneous movement. Proximal end 252 of clip 250 remains constrained by outer sheath 212. During the deployment process, apparatus 200 or any portion of apparatus 200 can be retracted while injecting contrast medium. Contrast medium can be injected through apparatus 200, or through a venous catheter or separate arterial catheter. Contact of the distal end 251 of clip 250 can be confirmed by visualizing bulging of either or both the venous wall 221 and the arterial wall 231 during a contrast medium injection.

Figure 8:
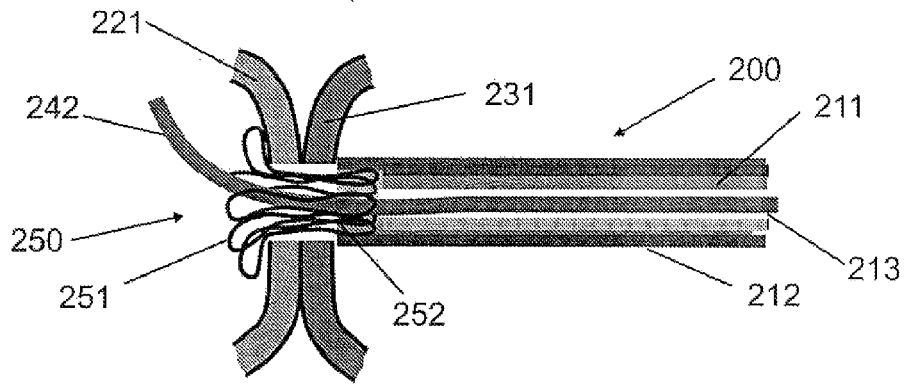
FIG. 8 is a cross sectional view of an anastomotic clip deployment device shown at a fistula creation site prior to full deployment of an anastomotic clip.

In FIG. 8, clip 250 has been further deployed, and outer sheath 212 retracted to expose venous wall 221 and arterial wall 231. In an alternative embodiment, outer sheath 212 does not pass through arterial wall 231 and/or venous wall 221 and clip 250 is pushed through both walls during deployment.

Figure 9:
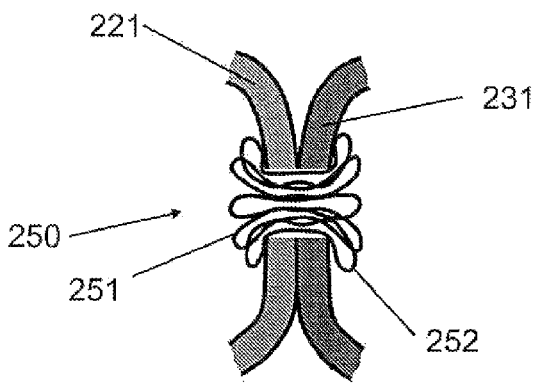
FIG. 9 is a cross sectional view of a fistula creation site with an anastomotic clip deployed.

FIG. 9 depicts a fully deployed clip 250, providing an anastomotic connection between arterial wall 231 and venous wall 221 such as to provide a flow path, or fistula, between an artery and vein such as an artery or vein in an arm or leg of the patient. Clip 250 can provide numerous functions as has been described hereinabove including but not limited to: scaffolding an opening between the first vessel and the second vessel; reducing neointimal proliferation into the fistula flow path; preventing tissue from protruding into the fistula flow path;

placing a portion of the first vessel wall in tension with the tissue of the second vessel wall; reducing bleeding of the tissue neighboring the fistula; enhancing healing of the tissue neighboring the fistula; and combinations thereof. In FIG. 9, guidewire 242 has been removed and the procedure can be considered complete. In a preferred embodiment, guidewire 242 remains in place, and subsequent operations can be performed to enhance the outcomes and/or therapeutic benefits of the procedure, or to complete one or more other interventional procedures such as those performed in either the starting vessel, or target vessel by way of the starting vessel. A flow measurement procedure, as has been described hereabove, may be performed, and flow adjusted such as through further dilation of clip 250. The cross-section of the flow thru lumen of clip 250 may be circular or oval and shape, and the dilating apparatus, such as a dilating balloon, have a similar cross-section. In an alternative, preferred embodiment, clip 250 has additional functionality to improve the long-term patency of the fistula or otherwise provide improved therapy to the patient. Improved functionality of clip 250 may include the integration of an agent, such as an antibacterial, antithrombogenic, anti-prolific, or other agent. Clip 250 may also a covering along a part or the entirety of its length, such as a covering consisting of one or more of: polytetrafluoroethylene; Dacron™ material; Nitinol™ alloy; stainless steel; urethane; polyethylene; silicone; carbon and carbon compounds.

During retraction of apparatus 200 or one of its components, a balloon integrated on the core 211 of apparatus 200, not shown, may be inflated to help bias clip 250 in an open position during retraction. Prior to complete retraction, a contrast medium injection from the arterial side can be used to assess blood flow through the fistula. In a preferred embodiment, guidewire 240 is not removed until proper flow and/or sufficient therapeutic benefit are confirmed. If flow is determined to be insufficient, or even too great, subsequent procedures can be employed to change the flow characteristics, such procedures described in more detail hereinbelow.

Figure 10:
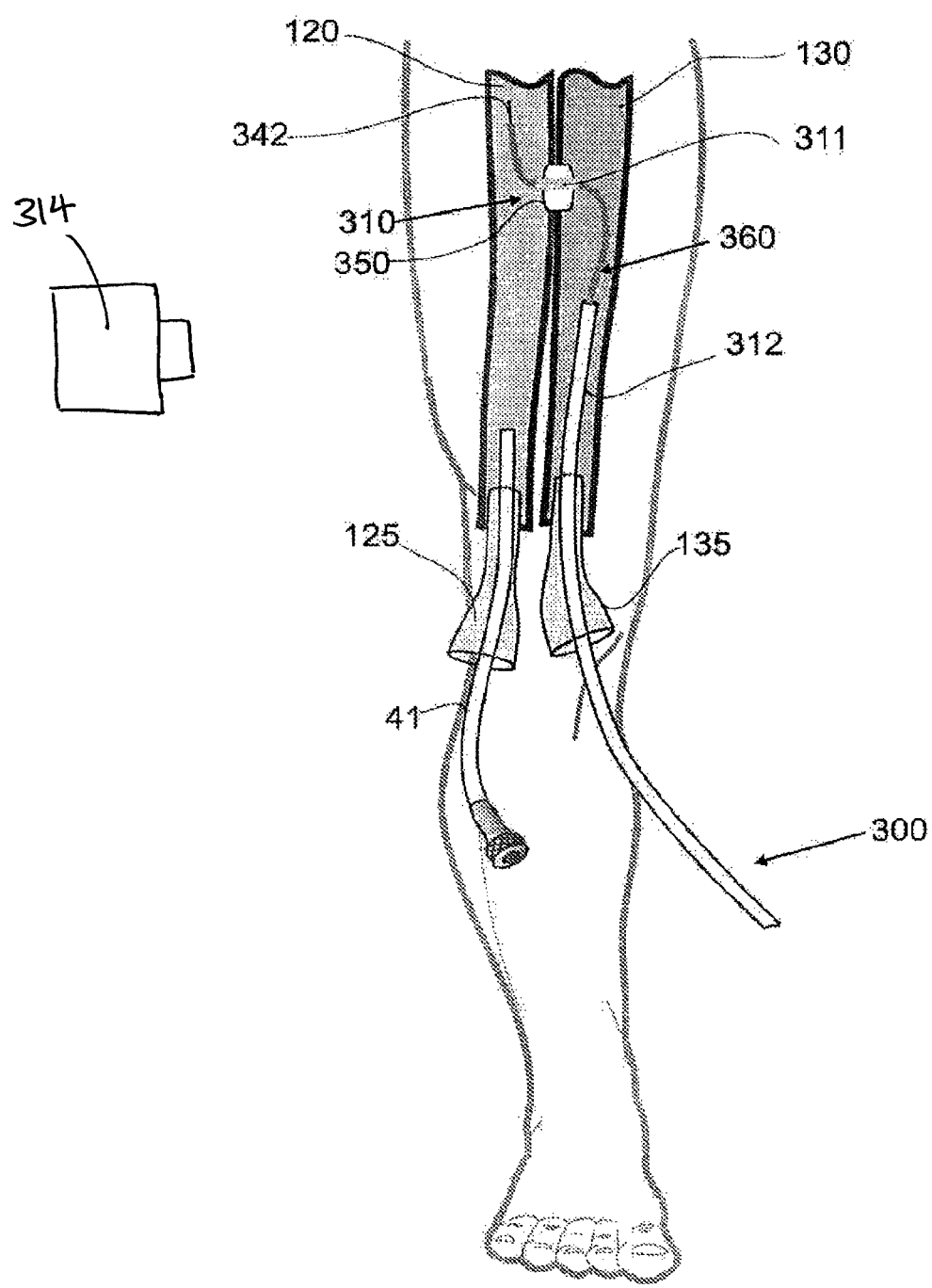
FIG. 10 illustrates a fistula treatment device, located in a fistula created in the thigh of the patient, with a consistent with the present invention.

FIG. 10 depicts a fistula modification procedure and apparatus such that flow through the fistula can be increased or decreased, or other characteristics of the fistula can be improved or otherwise modified to provide enhanced therapy to the patient. Shown in FIG. 10 is artery 130, such as the femoral artery, and vein 120 such as the femoral vein, located in the thigh of a patient, after a thigh-located fistula 310 has been created using one or more techniques described in detail throughout this application. Anastomotic clip 350 has been placed between artery 130 and vein 120 to provide and maintain long-term flow of highly oxygenated arterial blood into the venous system. Placed in a right femoral vein is venous introducer 125, and an imaging catheter 41 introduced through venous introducer 125 such that its tip resides at a location upstream to fistula 310. Inserted into the left femoral artery of the patient is arterial introducer 135, and fistula maintenance apparatus 300. Fistula maintenance apparatus 300 is placed over a guidewire, guidewire 342, which passes through fistula 310, from artery to vein, similar to the wires placed in the fistula creation procedures described hereinabove. In a preferred embodiment, guidewire 342 was the guidewire used to create fistula 310, and has remained in place since originally placed from artery 130 to vein 120. Alternatively, guidewire 342 can be placed using standard interventional guidewire techniques after fistula 310 has been created. A pigtail catheter or other contrast medium injection catheter, not shown, may be placed such that its tip is superior to fistula 310, to visualize fistula flow with contrast medium injections.

Apparatus 300 includes outer sheath 312 that slidingly receives one or more internal components within one or more internal lumens. Fistula treatment device 360 is a catheter device including an inner lumen surrounding guidewire 342 such that as either fistula treatment device 360 or apparatus 300 are advanced, the advancement tracks along guidewire 342. Fistula treatment device 360 includes near its distal end, fistula treatment element 311 that has been advanced to remain within the inner diameter of clip 350 of fistula 310. Fistula treatment element 311 can take numerous forms to increase or decrease the flow through fistula 310, modify the structure of clip 350 or fistula 310, add or remove material or agents from fistula 310 or clip 350, or otherwise modify one or more characteristics or properties of clip 350 or fistula 310.

In a preferred embodiment, fistula treatment element 311 is a balloon used to dilate clip 350 and fistula 310. Clip 350 may be constructed of plastically deformable materials, either totally or partially, such that dilation will expand those materials to a greater diameter. For example, clip 350 may include self-expanding material at its ends, and plastically deformable materials at its midsection that that dilation increased the diameter of the midsection and resultant fluid pathway at one or more locations along the fistula. Dilation of a fully self-expanding clip 350 may also be appropriate to allow further expansion of clip 350 due to expansion and/or deformation of the tissue that surrounds clip 350. Decrease in fistula flow can be accomplished by decreasing the diameter at one or more locations along the fistula, such as with a specialized device that pulls a portion of the midsection of clip 350 towards a smaller diameter.

In another preferred embodiment, fistula treatment element 311 may include deployment of a second implant, not shown, to increase or decrease flow properties, to provide one or more drugs or agents, or to otherwise modify the fistula and/or clip 350. Placement of a second implant may be used to enhance scaffolding, prevent bleeding, reduce lumen diameter and/or perform another function, and may also require multiple dilations to achieve the desired effect.

In another preferred embodiment, fistula treatment element 311 may include an element to perform one or more of the following functions: covering a portion of the anastomotic clip, applying an agent such as an anti-biotic agent, anti-infective agent and/or anti-proliferative agent, applying a source of heat, applying a source of cooling, applying a source of energy such as electrical energy including radio-frequency or microwave energy; cryogenic energy; light; and radiation.

Modification of fistula 310 may be performed during the same procedure that created fistula 310, such as within an hour of the creation of fistula 310 and over the same guidewire used to deploy clip 350, or the modification procedure can be performed in a subsequent procedure such as a procedure greater than twenty four hours from the creation of fistula 310. In such a subsequent procedure, a new guidewire, introduced through either artery 120 or vein 130 can be manipulated, using standard interventional techniques, to access the fistula and cross over to the connected vessel, either in the same direction as used in fistula creation or the opposite. Apparatus 300 can then be advanced over the vessel-to-vessel guidewire to perform the fistula modification or treatment procedure.

Additional and/or alternative flow modification procedures can be performed to increase or decrease flow of arterial blood into the venous system. For example, creation of a second fistula between the artery 130 and vein 120, second fistula not shown, can be made to increase flow of oxygenated blood to the venous system. The second fistula can be created during the same procedure as the first fistula creation procedure, such as within an hour of the first fistula creation, or in a subsequent procedure such as a procedure more than twenty-four hours from the creation of the first fistula. The flow modification procedure can be performed before the anastomotic clip is placed, or after it is in position between the artery and vein. The second fistula can alternatively be created in a different location, such as in the limb of the patient or at a more central location.

Flow modifications procedures may be performed for multiple reasons, such as reasons derived from a measurement of one or more physiologic parameters including but not limited to: blood pressure, heart rate, cardiac output, pa $O_2$, $O_2$ saturation, mean systemic arterial pressure or mean systemic venous pressure, respiration, blood glucose, heart rate variability or other heart or other physiologic parameter. The results of the analysis are compared to one or more clinical outcome target values or other types of outcome target values, such that if one or more targets are achieved, the procedure is complete and no flow modification procedures are performed at that time. If one or more target values are not achieved, a flow modification procedure may be performed. While this may be the last step of this assessment procedure, in a preferred embodiment, a repeat parameter measurement is performed, and flow modifications repeated, until target values have been achieved. One or more parameters can be measured and assessed in the method described hereinabove. A first parameter may be used for initial assessment, and a different for a subsequent assessment. Physiologic measurements can be assessed individually, or in combination with one or more other physiologic parameters. Outcome target values can be based on a single physiologic measurement and analysis, or a combination of multiple analyses to determine satisfactory flow conditions. The flow modifications can be performed multiple times. Target levels can be adjusted based on patient condition, procedure time or other procedure parameter (e.g. amount of contrast medium used), or amount of flow modifications performed. Other variables and parameters can be integral to or other otherwise impact the flow modification procedures including but not limited to: patient disease state, first outcome target level, second outcome target level, duration of procedure, number of flow modification procedures performed, outcome of previous analysis of physiologic data, outcome of analysis of different set of physiologic data, patient age or other patient parameter.

In a preferred embodiment, fistula maintenance apparatus 300 of FIG. 10 includes a visualization element such as an external ultrasound element 314. The visualization element may also be an ultrasound catheter, such as a rotational or fixed array ultrasound catheter, which is inserted in a lumen of fistula maintenance apparatus 300, or may be an integrated ultrasound device has as an array of ultrasound crystals which are fixedly mounted along the distal portion of fistula maintenance apparatus 300 and contain electronic connections that are connected to a proximal handle of fistula maintenance apparatus 300 and mate with a standard ultrasonic viewing monitor, all not shown. In an alternative or additional preferred embodiment, fistula maintenance apparatus 300 of FIG. 10 includes one or more visualization markers, such as radiographic markers or embedded agents, or ultrasound markers, all not shown. These markers can be used to perform controlled advancements, retractions, rotations and other positioning of fistula maintenance apparatus 300 during the fistula creation procedure.

In a preferred embodiment, fistula maintenance apparatus 300 is used to modify an existing dialysis fistula. Apparatus 300 is used to improve flow conditions, such as to increase or decrease fistula flow after a flow measurement procedure has been performed and sub-optimal flow determined. To reduce flow, apparatus 300 may be used to place an implant to narrow a portion of the flow path, either intra-luminally or extra-luminally. If the dialysis fistula includes an artificial graft, a flow-impinging implant may be placed along side of the graft or a luminal narrowing device placed within the graft. To increase flow, apparatus 300 may dilate a portion of the flow path, and/or remove a narrowing device or some flow-narrowing tissue.

Figure 11A:
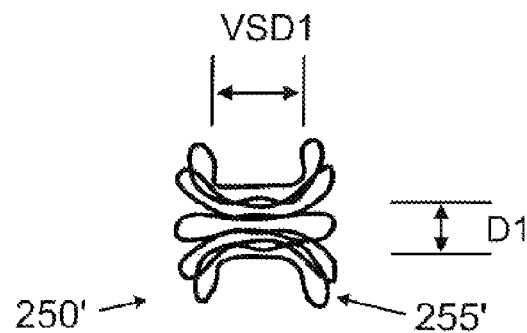
FIG. 11a illustrates an anastomotic clip consistent with the present invention.
Figure 11B:
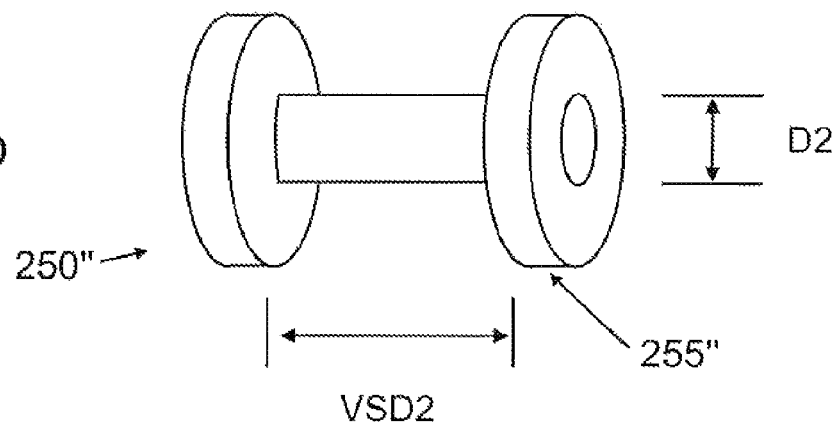
FIG. 11b illustrates another anastomotic clip consistent with the present invention.
Figure 11C:
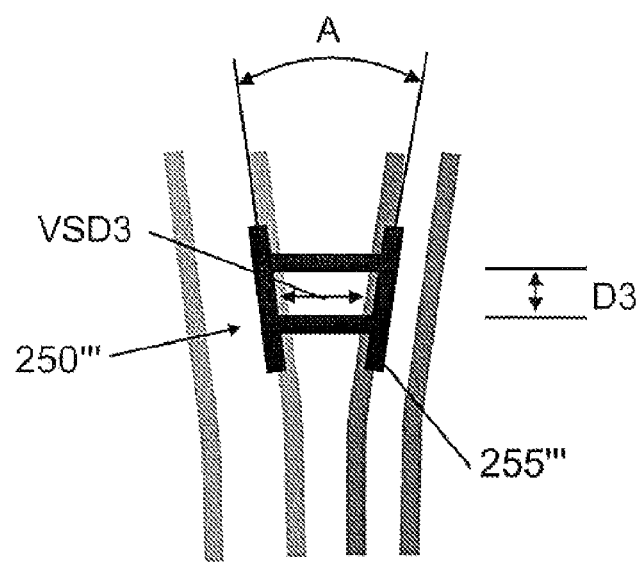
FIG. 11c illustrates yet another anastomotic clip consistent with the present invention.

FIGS. 11a, 11b and 11c depict different configurations of anastomotic clips consistent with the present invention, each providing different properties and configurations applicable to fistula site, patient anatomy and other patient parameter specifics. The fistulas of the present invention may be placed in one or more limbs or other locations within the patient and need to be designed and manufactured to support a wide range of anatomical geometries and other physiologic factors to support a substantial patient population afflicted with COPD and other applicable disease states. Implants will be needed to support a range of artery diameters, vein diameters, and distance between the lumens of the appropriate arteries and veins. Implants with a varied range of elastic forces, scaffolding surface areas, and flange geometries may be required depending on the tissue and tissue properties surrounding the fistula, including the muscular nature of vessel walls. Implants may also need to support varied ranges of: distance from an arterial side branch; distance from an arterial side branch; arterial flow; venous flow; wall thickness of artery; wall thickness of vein; degree of calcification of artery; degree of calcification of vein; geometric relationship between the artery and vein lumens at the fistula site; hemodynamic factors; and other factors.

Referring specifically to FIG. 11a, anastomotic clip 250' has a similar configuration to anastomotic clip 250 of FIGS. 6 through 9 is shown. Clip 250', a continuous wire construction, has a flange 255' at each end, separated by length VSD1. Clip 250' has luminal diameter D1. Clip 250' may be chosen for implantation in a therapeutic fistula of the present invention based on numerous properties including but not limited to: length VSD1; diameter D1; elastic properties of the clip; plastic properties of the clip; vessel tensioning forces; and other properties chosen to correlate to the patient's anatomy and the fistula requirements. Length VSD1 correlates to the vessel separation distance at the fistula site. Diameter D1 correlates to the intended luminal diameter of the fistula.

Clip 255", a dumbbell construction with a solid flow through lumen, has a flange 255" at each end, separated by length VSD2. Clip 250" has luminal diameter D2. Clip 250" may be chosen for implantation in a therapeutic fistula of the present invention based on numerous properties including but not limited to: length VSD1; diameter D1; covered nature of flow through lumen; rigidity of the clip; plastic properties of the clip; vessel tensioning forces; and other properties chosen to correlate to the patient's anatomy and the fistula requirements. Length VSD2 correlates to the vessel separation distance at the fistula site. Diameter D2 correlates to the intended luminal diameter of the fistula.

Clip 255''', a wire framed construction with non-parallel flanged ends, has a flange 255''' at each end, separated by length VSD3. Clip 250''' has luminal diameter D3 and relative angle between each flange 255" is angle A. Clip 250''' may be chosen for implantation in a therapeutic fistula of the present invention based on numerous properties including but not limited to: angular alignment of the artery and vein at fistula location; length VSD3; diameter D3; rigidity of the clip; plastic properties of the clip; vessel tensioning forces; and other properties chosen to correlate to the patient's anatomy and the fistula requirements. Length VSD2 correlates to the vessel separation distance at the fistula site. Diameter D2 correlates to the intended luminal diameter of the fistula. Angle A correlates to the angular alignment of the artery and vein at the fistula location.

In a preferred embodiment, a kit is provided with multiple anastomotic clips such as clips 255', 255" and 255'" of FIGS. 11a, 11b and 11c. The clinician or other associated health care professional chooses which particular anastomotic clip to place in the therapeutic fistula of the present invention based on numerous physiologic parameters including vascular geometry, vascular characteristics, and other patient or therapy specific parameters such as those that can be measured or diagnosed pre-procedurally or intra-procedurally.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating chronic obstructive pulmonary disease in a patient comprising:
   externally visualizing anatomical structures in a limb of the patient to determine a degree of calcification;
   selecting a first anatomical structure and a second anatomical structure in the limb based at least in part on the degree of calcification;
   creating a fistula in the limb between a first anatomical structure and a second anatomical structure at a location based at least in part on the degree of calcification;
   wherein the first anatomical structure contains blood at a first oxygen content level and the second anatomical structure contains blood at a second oxygen content level, said first oxygen content level greater than said second oxygen content level; and
   wherein the second anatomical structure provides blood to a lung of the patient.

2. The method of claim 1 wherein the fistula is created in a surgical procedure.

3. The method of claim 1 wherein the fistula is created in an interventional procedure.

4. The method of claim 1 wherein the performance of said method decreases systemic vascular resistance of the patient.

5. The method of claim 1, wherein said treatment is based on an increase of the partial pressure of O2 dissolved in the arterial blood plasma, an increase of the hemoglobin O2 saturation in arterial or venous blood, or an increase of the O2 concentration in arterial or venous blood.

6. The method of claim 1 further comprising creating a second fistula between a third anatomical structure and a fourth anatomical structure wherein the third anatomical structure contains blood at a first oxygen content level and the fourth anatomical structure contains blood at a second oxygen content level, said first oxygen content level greater than said second oxygen content level.

7. The method of claim 6 wherein the second fistula is created in a limb of the patient.

8. The method of claim 1 further comprising placing a guidewire between the first anatomical structure and the 2nd anatomical structure.

9. The method of claim 1 further comprising dilating the fistula.

10. The method of claim 1 further comprising inserting an anastomotic implant within the fistula.

11. The method of claim 10 further comprising placing a second anastomotic implant within the fistula.

12. The method of claim 10 further comprising dilating the fistula after the anastomotic implant is placed.

13. The method of claim 1 further comprising the step of applying energy to the fistula.

14. The method of claim 13 wherein the energy is selected from the group consisting of: electrical energy such as radiofrequency or microwave energy; cryogenic energy; heat; radiation; and combinations thereof.

15. The method of claim 1 further comprising delivering an agent to the tissue neighboring the fistula.

16. The method of claim 15 wherein the agent is selected from the group consisting of: anti-proliferatives; anti-biotics; anti-thrombogenics; and combinations thereof.

17. The method of claim 1 further comprising performing a blood flow measurement procedure.

18. The method of claim 17 wherein the blood flow measurement procedure is performed prior to, after, or both prior to and after the creation of the fistula.

19. The method of claim 17 wherein a flow measurement procedure is performed after the creation of the fistula, and a flow modification procedure is performed.

20. The method of claim 19 wherein said flow modification procedure includes dilating the fistula.

21. The method of claim 19 wherein said flow modification procedure includes placing an anastomotic implant within the fistula.

22. The method of claim 1 wherein the fistula location is further based on an artery with at least a 2 mm diameter.

23. The method of claim 22 wherein the fistula location is based on a vein with at least a 3 mm diameter.

24. The method of claim 1 wherein the fistula location is further based on a vessel separation of less than 20 mm.

25. The method of claim 1 wherein blood flows through the fistula at a flow rate of at least 5 ml/min.

26. The method of claim 1 wherein the first anatomical structure is an artery.

27. The method of claim 26 wherein the anastomotic implant provides a function selected from the group consisting of: scaffolding an opening between the first vessel and the second vessel; reducing neointimal proliferation into the fistula flow path; preventing tissue from protruding into the fistula flow path; placing a portion of the first vessel wall in tension with the tissue of the second vessel wall; reducing bleeding of the tissue neighboring the fistula; enhancing healing of the tissue neighboring the fistula; and combinations thereof.

28. The method of claim 26 wherein the artery is less than 4 mm in diameter.

29. The method of claim 1 wherein the second anatomical structure is a vein.

30. The method of claim 29 wherein the vein is selected from the group consisting of: saphenous; femoral; iliac; popliteal; brachial; basilic; cephalic; medial forearm; medial cubital; axillary; and jugular.

31. The method of claim 29 wherein the vein is less than 4 mm in diameter.

32. The method of claim 1 wherein the fistula has a circular cross section when said method is completed.

33. The method of claim 1 wherein the fistula has an oval cross section when said method is completed.

34. The method of claim 1 further comprising the step of placing an anastomotic implant between the first anatomical structure and the second anatomical structure.

35. The method of claim 34 wherein the anastomotic implant provides a function selected from the group consisting of: scaffolding an opening between the first anatomical structure and the second anatomical structure; reducing neointimal proliferation into a fistula flow path; preventing tissue from protruding into a fistula flow path; placing a portion of a wall of the first anatomical structure in tension with the tissue of a wall of the second anatomical structure; reducing bleeding of the tissue neighboring the fistula; enhancing healing of the tissue neighboring the fistula; and combinations thereof.

36. The method of claim 34 wherein the anastomotic implant includes an agent selecting from the group consisting of: anti-bacterial; anti-thrombogenic; anti-prolific; and combinations thereof.

37. The method of claim 34 wherein the anastomotic implant includes a covered portion along its length.

38. The method of claim 37 wherein the covering is selected from the group consisting of: polytetrafluoroethylene; Dacron material; Nitinol alloy; stainless steel; and combinations thereof.

* * * * *